(12) United States Patent
Murakami

(10) Patent No.: US 8,491,873 B2
(45) Date of Patent: Jul. 23, 2013

(54) DENTIFRICE

(75) Inventor: Yoshinori Murakami, Sumida-ku (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/322,752

(22) PCT Filed: May 28, 2010

(86) PCT No.: PCT/JP2010/003589
§ 371 (c)(1),
(2), (4) Date: Nov. 28, 2011

(87) PCT Pub. No.: WO2010/140328
PCT Pub. Date: Dec. 9, 2010

(65) Prior Publication Data
US 2012/0070387 A1   Mar. 22, 2012

(30) Foreign Application Priority Data
Jun. 4, 2009  (JP) .................. 2009-135510

(51) Int. Cl.
*A61Q 11/00* (2006.01)
*A61K 8/00* (2006.01)
*A61K 8/25* (2006.01)

(52) U.S. Cl.
USPC ................... 424/49; 424/401; 424/52

(58) Field of Classification Search
USPC ............................. 424/49, 401, 52
See application file for complete search history.

(56) References Cited

U.S. PATENT DOCUMENTS

| 5,882,631 A * | 3/1999 | Suga et al. ...................... 424/49 |
| 2004/0247533 A1 | 12/2004 | Hosoya et al. |
| 2007/0059256 A1 | 3/2007 | Kato |

FOREIGN PATENT DOCUMENTS

| EP | 2 045 248 A1 | 4/2009 |
| JP | 2002-047158 A | 2/2002 |
| JP | 2003-238372 A | 8/2003 |
| JP | 2004-284956 A | 10/2004 |
| JP | 2005-247869 A | 9/2005 |
| JP | 2006-003989 A1 | 1/2006 |
| JP | 2006-117598 A | 5/2006 |
| JP | 2007-70258 A | 3/2007 |
| JP | 2007-291021 A | 11/2007 |
| JP | 2008-24652 A | 2/2008 |
| JP | 2008-88145 A | 4/2008 |

OTHER PUBLICATIONS

Specialty Minerals, "ViCALity Extra Heavy" USP/FCC Precipitated Calcium Carbonate, 2000, pp. 1-2.*
International Search Report (ISR) for PCT/JP2010/003589, I.A. fd: May 28, 2010, mailed Jul. 20, 2010 from the Japanese Patent Office, Tokyo, Japan.
International Preliminary Report on Patentability (Chapter I of the Patent Cooperation Treaty) for PCT/JP2010/003589, I.A. fd: May 28, 2010, issued Jan. 17, 2012, from the International Bureau of WIPO, Genera, Switzerland.

* cited by examiner

*Primary Examiner* — Lezah Roberts
(74) *Attorney, Agent, or Firm* — Sterne, Kessler, Goldstein & Fox P.L.L.C.

(57) ABSTRACT

Provided is a dentifrice which exhibits sufficient shape retentivity even when a polymer-based binder is not incorporated, which does not leave a taste or white residues even when the amount of powder incorporated is small, and which has satisfactory dispersibility in the oral cavity and a light feeling of use.
A dentifrice containing the following components (A), (B) and (C):
(A) 0.1 to 10% by mass of a thickening silica having an oil absorption of 150 to 500 mL/100 g,
(B) 0.1 to 8 % by mass of heavy calcium carbonate, and
(C) 40 to 70 % by mass of water at a mass ratio (B:A) of the component (B) and the component (A) of 2:1 to 0.5:99.5.

8 Claims, No Drawings

DENTIFRICE

FIELD OF THE INVENTION

The present invention relates to a dentifrice having a satisfactory feeling of use.

BACKGROUND OF THE INVENTION

In many dentifrices, abrasives are incorporated for the purpose of removing dental plaque or colored materials. Examples of the abrasives that are widely used include calcium carbonate, calcium hydrogen phosphate, abrasive silica, and aluminum hydroxide. On the other hand, a dentifrice is demanded to give appropriate viscoelasticity and shape, for the purposes of the ease of applying a dentifrice to a toothbrush, dispersibility in the oral cavity, productivity, and retentivity on the tooth surface. Thus, a binder is incorporated for that purpose. Examples of the binder that may be used include water-soluble polymers represented by carboxymethyl cellulose sodium, and clay minerals such as bentonite. Therefore, dentifrices which include an abrasive such as calcium carbonate and a binder in combination, have also been reported (Patent Documents 1 to 3)

PRIOR ART DOCUMENT PATENT DOCUMENT

Patent Document 1: JP-A-2002-47158
Patent Document 2: JP-A-2006-117598
Patent Document 3: JP-A1-2006-3989

SUMMARY OF THE INVENTION

However, dentifrices containing conventional binders have excellent shape retentivity, but on occasions, the dentifrices have a heavy feeling, do not have sufficient dispersibility in the oral cavity, and do not sufficiently render the action of antibacterial components or fragrance components. Furthermore, when a dentifrice is given shape retentivity by decreasing the binder and increasing powder components, there is a problem that the taste may be deteriorated, or when attached in the surroundings of the oral cavity, the dentifrice easily remains as white residues.

Therefore, it is an object of the present invention to provide a dentifrice which has a light feeling of use and sufficient shape retentivity, and has an excellent feeling of use with satisfactory dispersibility in the oral cavity.

Thus, the inventors of the present invention conducted an investigation to develop a dentifrice having a light feeling of use as well as high shape retentivity, and they found that when heavy calcium carbonate and thickening silica are incorporated at certain proportions, a dentifrice exhibiting sufficient shape retentivity regardless of whether the water content is high may be obtained.

That is, the present invention provides a dentifrice containing the following components (A), (B) and (C)
(A) 0.1 to 10% by mass of a thickening silica having an oil absorption of 150 to 500 mL/100 g,
(B) 0.1 to 8% by mass of heavy calcium carbonate, and
(C) 40 to 70% by mass of water,
wherein the mass ratio (B:A) of the component (B) and the component (A) is 2:1 to 0.5:99.5.

EFFECT OF THE INVENTION

The dentifrice of the present invention exhibits high shape retentivity regardless of whether the water content is high, and since the amount of powder is not large, the dentifrice has a satisfactory taste and white residues do not remain Furthermore, the dentifrice has satisfactory dispersibility in the oral cavity, and has a light feeling of use which is not found in conventional dentifrices. Furthermore, large amounts of antibacterial components, water-soluble fluorides, water-soluble medicinal ingredients and the like can be incorporated into the dentifrice of the present invention.

MODES FOR CARRYING OUT THE INVENTION

The dentifrice of the present invention contains (A) a thickening silica having an oil absorption of 150 to 500 mL/100 g. The thickening silica is a silica having a larger oil absorption than the conventional silica that is incorporated into dentifrices as abrasive silica. When thickening silica and heavy calcium carbonate are dispersed in water at certain proportions, a hydrogel containing a large amount of water is formed, and the gel exhibits satisfactory shape retentivity as a dentifrice. Even when a silica having an oil absorption of less than 150 mL/100 g and heavy calcium carbonate are used in combination, sufficient shape retentivity cannot be obtained. An oil absorption, from the viewpoint of shape retentivity, is preferably 200 to 400 mL/100 g, and more preferably 250 to 380 mL/100 g. As the thickening silica, commercially available products such as SYLOPURE25 manufactured by Fuji Silysia Chemical, Ltd., and SOREOSILTC 15 manufactured by Crosfield Chemicals, Inc. can be used. The oil absorption can be measured by a method according to JIS K5101-13-2. Furthermore, the average particle size of the thickening silica used is preferably 1 to 10 him, more preferably 1.5 to 8 μm, and even more preferably 2 to 8 μm.

From the viewpoints of appropriate shape retentivity, dispersibility in the oral cavity, and the feeling of use, the content of the (A) thickening silica in the dentifrice of the present invention is preferably 0.1 to 10% by mass, more preferably 0.5 to 8% by mass, even more preferably 2 to 8% by mass, even more preferably 3% to by mass, and even more preferably 3 to 8% by mass.

The (B) heavy calcium carbonate used in the dentifrice of the present invention forms a gel together with the component (A), but it also functions as an abrasive. The (B) heavy calcium carbonate is commercially available as calcium carbonate and is also used as a food additive. The heavy calcium carbonate is not a product based on a chemical synthesis reaction, but refers to a white powder obtained by selecting limestone, seashells and the like containing calcium carbonate, cleaning the materials, and pulverizing the materials. The average particle size of the heavy calcium carbonate used in the present invention is preferably 0.1 to 50 μm, and more preferably 1 to 10 μm.

The content of the (B) heavy calcium carbonate in the dentifrice of the present invention is 0.1 to 8% by mass, more preferably 0.5 to 8% by mass, and even more preferably 1 to 7% by mass, from the viewpoints of appropriate shape retentivity, taste (no powderiness), and the feeling of use. Furthermore, the sum of the contents of the component (B) and the component (A) is preferably 5 to 18% by mass, more preferably 5 to 15% by mass, and even more preferably 7 to 15% by mass, from the viewpoints of shape retentivity and scenting.

Furthermore, for the dentifrice of the present invention, when the mass ratio (B:A) of the component (B) and the component (A) falls within a scope ranging 2:1 to 0.5:99.5, a gel which contains a large amount of water and exhibits shape retentivity is formed. When the content of the (B) heavy calcium carbonate is reduced, and shape retentivity is maintained, the taste, white residues, and the dispersibility in the oral cavity are made satisfactory, the weight ratio B:A is more preferably 3:2 to 1:9.9, even more preferably 5:5 to 1.99, and even more preferably 5:6. to 1:99.

In regard to the dentifrice of the present invention, since the gel formed from the component (A) and the component (B) contains a large amount of water and exhibits satisfactory shape retentivity, the dentifrice can contain water at a proportion of 40 to 70% by mass. Since the dentifrice exhibits satisfactory shape retentivity despite containing such a large amount of water, the dentifrice of the present invention has satisfactory dispersibility in the oral cavity and has a light and satisfactory feeling of use. The content of water is more preferably 45 to 70% by mass, and even more preferably 50 to 70% by mass In addition, the content of water in the dentifrice of the present invention includes the water contained in the incorporated components such as a sorbitol solution, and water that is separately incorporated.

The amount of water in the dentifrice composition can be calculated from the amount of water incorporated and the amount of water in the incorporated components, but can also be measured with, for example, a Karl-Fischer moisture meter. As the Karl-Fischer moisture meter, for example, a trace moisture analyzer (Hiranuma Sangyo Corporation) can be used. With this apparatus, 5 g of a dentifrice composition is taken and suspended in 25 g of anhydrous methanol, and 0.02 g of this suspension is separated, to thereby measure the amount of moisture.

The mass ratio (A:C) of the component (A) and the component (C) in the dentifrice of the present invention is preferably 1:7 to 1:20, and more preferably 1:8 to 1:20, from the viewpoint of powderiness.

The dentifrice of the present invention can contain, in addition to the components as mentioned above, an abrasive other than heavy calcium carbonate, a surfactant, a binder, a wetting agent, a flavor, a sweetener, an antibacterial agent, an antiseptic agent, a water-soluble fluoride, a pH adjusting agent, various medicinal ingredients, and the like as necessary, to the extent that the effects of the present invention are not impaired.

Here, examples of the abrasive include hydrated silica, anhydrous silica having an oil absorption of 50 to 120 mL/100 q, calcium hydrogen phosphate for dentifrices, calcium pyrophosphate, insoluble potassium metaphosphate, aluminum silicate, zirconium silicate, bentonite, zeolite, aluminum oxide, aluminum hydroxide, and resins.

As the surfactant, anionic surfactants, nonionic surfactants, cationic surfactants, and amphoteric surfactants are used. These surfactants may be used such that only one of an anionic surfactant, a nonionic surfactant and the like may be used, but in the case of using two or more surfactants, it is preferable to use any one of the surfactants in an amount of 0.1% by mass or less. Furthermore, when only one of the aforesaid surfactants is used, for example, if the dentifrice contains an anionic surfactant, an anionic surfactant of plural compositions can be used therefor, and surfactants of plural compositions for two or more surfactants can be used.

Examples of the anionic surfactant include acylamino acid salts such as sodium acylglutamate and sodium acylsarcosinate; alkyl phosphates such as sodium alkyl phosphate; alkyl sulfuric acid ester salts, higher fatty acid sulfonated monoglyceride salts; fatty acid ester salts of isethionic acid. N-methyl long-chain acyltaurine sodium salts; and polyoxyethylene monoalkyl phosphates. The alkyl groups and acyl groups of the hydrophobic groups in these anionic surfactants preferably have 6 to 18 carbon atoms, and more preferably 10 to 14 carbon atoms. Furthermore, sodium salts are preferred as their salts. As the anionic surfactant, alkyl sulfuric acid ester salts are more preferred from the viewpoints of having good foamability and being available at low costs.

The anionic surfactant is preferably contained in the dentifrice of the present invention in an amount of 0 to 5% by mass, and more preferably 0.1 to 3% by mass Examples of the nonionic surfactant include polyoxyalkxylene adduct surfactants, amine oxide surfactants, mono- or diethanolamide surfactants, sorbitan fatty acid esters, glycerin fatty acid esters, polyglycerin fatty acid esters, and sucrose fatty acid esters. Among these, sorbitan fatty acid esters, glycerin fatty acid esters, polyglycerin fatty acid esters, and sucrose fatty acid esters are preferred, and polyglycerin fatty acid esters such as decaglycerin monostearate, and pentaglycerin monomyristate are more preferred. In the present invention, one or more of these can be used.

The content of the nonionic surfactant is preferably 0.1 to 30% by mass, and. more preferably 0.2 to 10% by mass, in the dentifrice composition of the present invention.

Here, examples of the binder include sodium alginate, carboxymethyl cellulose sodium, carrageenan, xanthan gum, sodium polyacrylate, hydroxyethyl cellulose, hydroxypropyl cellulose, pectin, tragacanth gum, gum arabic, guar gum, gum karaya, locust beam gum, gellan gum, tamarind gum, psyllium seed gum, polyvinyl alcohol, sodium chondroitin sulfate, and methoxyethylene-maleic anhydride copolymers. Particularly, carboxymethyl cellulose sodium, carrageenan, and xanthan arum are preferred. These substances may be used singly or in combination of two or more kinds. These binders are preferably contained in an amount of 0.01 to 3% by mass, and more preferably 0.1 to 2% by mass, in the dentifrice.

Examples of the wetting agent include polyethylene glycol, propylene glycol, sorbitol, glycerin, 1,3-butylene glycol, maltitol, lactitol, xylitol, and trehalose. Among them, sorbitol and glycerin are preferred.

Examples of the flavor include synthetic flavors such as l-menthol, carvone, anethole, eugenol, limonene, ocimene, n-amyl alcohol, citronellol, α-terpineol, methyl salicylate, methyl acetate, citronellol acetate, cineole, 1,8-cineol, linalool, ethyl linalool, vanillin, and thymol; and natural flavors such as spearmint oil, peppermint oil, rosemary oil, cinnamon-bark oil, pimento oil, perilla oil, menthol oil, aniseed oil, wintergreen oil, wintergreen oil, sassafras oil, clove oil, sage oil, eucalyptus oil, marjoram oil, cinnamon oil, thyme oil, lemon oil and orange oil.

Examples of the antibacterial agent include salts of chlorhexidine, cetylpyridinium chloride, benzaikonium chloride, and benzethonium chloride.

Examples of the antiseptic agent include benzoic acid, sodium benzoate, parahydroxybenzoic acid, and parahydroxybenzoic acid esters.

Examples of the various medicinal ingredients include anti-inflammatory agents such as aluminum chlorhydroxy allantoinate, azulene, glycyrrhetinic acid, epidihydrocholesterin, α-bisabolol, glycyrrhizic acid, and salts thereof; phenolic compounds such as hinokitiol; anti-plasmin agents such as tranexamic acid, and ε-aminocaproic acid; α-tocopherol, α-tocopherol acetate (dl-form and d-form) and salts thereof; copper compounds such as sodium copper chlorophyllin and copper gluconate; salts such as sodium chloride and potassium nitrate; enzymes such as dextranase, mutanase, amylase, and lysozyme chloride; extracts of *Angelica acutiloba*, phellodendron bark, clove, scutellaria root, safflower and the like; aluminum lactate, strontium chloride, berberine, hydroxamic acid and derivatives thereof, sodium tripolyphosphate, zeolite, dihydrocholesterol, and zinc citrate. Among them, glycyrrhetinic acid, glycyrrhizic acid, and salts thereof; copper compounds such as sodium copper chlorophyllin and copper gluconate; salts such as sodium chloride and potassium nitrate; and water-soluble medicinal ingredients such as strontium chloride and derivatives thereof and sodium tripolyphosphate are preferred.

Examples of the water-soluble fluoride include sodium fluoride, tin fluoride, ammonium fluoride, potassium fluoride, lithium fluoride, sodium monofluorophosphate, potassium monofluorophosphate, and ammonium fluoride. Sodium monofluorophosphate and potassium monofluorophosphate are preferred.

The dentifrice of the present invention is a dentifrice that can be discharged on a toothbrush, and can be prepared in the form of a gel-like dentifrice or a toothpaste. It is preferable to prepare the dentifrice of the present invention in the form of toothpaste. The pH is preferably 4 to 11, and more preferably 5 to 10. Furthermore, when the dentifrice is prepared in the form of toothpaste, the viscosity (25° C.) is 800 to 5000 dPa·s, more preferably 1000 to 4000 dPa·s, and even more preferably 1000 to 3000 dPa·s, from the viewpoints of a light feeling of use, and the balance between dispersibility in the oral cavity and shape retentivity.

EXAMPLES

Hereinafter, the present invention will be described in detail by way of Examples.

(Measurement of Oil Absorption)

The oil absorption of the thickening silica (silicic anhydride) is measured by measuring the amount of boiled linseed oil that is absorbed by silicic anhydride by a method according to JIS K5101-13-2. Specifically, while boiled linseed oil is added dropwise to silicic anhydride that is to be analyzed, the components are kneaded with a steel spatula. The time point when the entire mixture can be wound around the steel spatula in a helical form is designated as an endpoint, and the amount of the boiled linseed oil that is absorbed is specified. The boiled linseed oil specified in JIS K5421 is used.

(Measurement of Viscosity)

The viscosity was measured with a Helipath viscometer (TVB-10R manufactured by Toki Sangyo Co., Ltd.) under the measurement conditions of a measurement temperature of 25° C., a rotor C, and a speed of rotation of 2.5 rpm for one minute.

Test Example 1

The gel forming ability of combinations of calcium carbonate (average particle size 6 μm) (Calci F9860 manufactured by Sankyo Seifun Co., Ltd.) with silica products having different oil absorptions were tested. Silica 1 (oil absorption 300 mL/100 g, average particle size 4 μm), silica 2 (oil absorption 70 mL/100 g, average particle size 10 μm), and silica 3 (granules average particle size 250 μm) were used. Calcium carbonate and silicas 1 to 3 were introduced into a bottle having a capacity of 120 mL in the amounts indicated in Table 1, together with 90 mL of ion exchanged water, and the ingredients were mixed. At this time, the height (mm) of the white area generated as a result of gel formation was measured. The results are presented in Table 1.

TABLE 1

(% by mass)

|  | Silica 1-calcium carbonate | Silica 2-calcium carbonate | Silica 3-calcium carbonate | Silica 1 | Silica 2 | Silica 3 | Calcium carbonate |
|---|---|---|---|---|---|---|---|
| Calcium carbonate (*1) | 5 | 5 | 5 | — | — | — | 10 |
| Silica (silicic anhydride) 1 | 5 | — | — | 10 | — | — | — |
| Silica (silicic anhydride) 2 | — | 5 | — | — | 10 | — | — |
| Silica (silicic anhydride) 3 | — | — | 5 | — | — | 10 | — |
| Ion-exchanged water | 90 | 90 | 90 | 90 | 90 | 90 | 90 |
| Total | 100 | 100 | 100 | 100 | 100 | 100 | 100 |
| Height two days after preparation (mm) | 42 | 13 | 11 | 25 | 13 | 20 | 8 |

(*1) Calci-F9860 by Sankyo Seifun Co., Ltd.

As is obvious from Table 1, it is understood that when silica 1 (thickening silica) and calcium carbonate are used in combination, gel formation occurs remarkably.

Test Example 2

Next, an investigation was conducted on the relationship between the gel forming ability of a combination of calcium carbonate and thickening silica, and the amount ratios of the combination. The test was conducted in the same manner as in Test Example 1.

TABLE 2

(% by mass)

| | Amount ratio (calcium carbonate:silica) | | | | | | | | | | |
|---|---|---|---|---|---|---|---|---|---|---|---|
| | 10:0 | 9.5:0.5 | 8:2 | 2:1 | 3:2 | 1:1 | 1:4 | 1:19 | 1:39 | 1:99 | 0:10 |
| Calcium carbonate (*1) | 10 | 9.5 | 8 | 6.7 | 6 | 5 | 2 | 0.5 | 0.25 | 0.1 | 0 |
| Silica (silicic anhydride) 1 | 0 | 0.5 | 2 | 3.3 | 4 | 5 | 8 | 9.5 | 9.75 | 9.9 | 10 |
| Ion-exchanged water | 90 | 90 | 90 | 90 | 90 | 90 | 90 | 90 | 90 | 90 | 90 |
| Total | 100 | 100 | 100 | 100 | 100 | 100 | 100 | 100 | 100 | 100 | 100 |
| Height two days after preparation (mm) | 8 | 13 | 23 | 31 | 35 | 42 | 46 | 52 | 50 | 48 | 20 |

(*1) Calci-F9860 by Sankyo Seifun Co., Ltd.

As a result, in the case of calcium carbonate (B): thickening silica (A)=8:2 to 1:99, the amount of gel formation was larger than, a test liquid containing silica (silicic anhydride 1) only. Calcium carbonate has excellent gel forming ability even in a small amount of addition, and the upper limit of the ratio B:A is satisfactory even at 0.5:99.5. From this test example, it was recognized that in the case of the ratio of B:A=2:1 to 1:99, the amount of gel formation was 1.5 or more times the amount of gel formation of the test liquid containing silica (silicic anhydride 1) only, and it was also recognized that in the case of 5:5 to 1:99, the amount of gel formation was 2 or more times the amount of gel formation of the test liquid containing silica (silicic anhydride 1) only. Thus, it is understood that the ratios are satisfactory.

Test Example 3

Toothpastes indicated in Table 3 were prepared, and evaluations were conducted on the shape retentivity (toothpaste height, and dripping from the toothbrush), white residues, viscosity, and taste.

The toothpaste height was evaluated by squeezing out the toothpaste from a tube having a discharge port with an opening diameter (internal diameter) of 8 mm, to a length of about 1.5 cm, and measuring the height (mm) after 3.0 seconds. The dripping from the toothbrush was evaluated by observing, 30 seconds after squeezing out the toothpaste on the toothbrush, whether the toothpaste dripped from the top surface formed at the tips of the brush hair to the lower part of the external side of the brush hair. The white residues were evaluated by spreading about 0.1 g of the dentifrice on the back of the hand of a person in a circle having a diameter of about 20 mm, and observing the change in the whiteness after 10 minutes. The taste was determined from the powderiness at the time of tooth brushing, and the scent was determined from the diffusibility of both the scent generated when the dentifrice was applied onto the toothbrush to use and the scent generated in the oral cavity. The evaluation of scenting was performed by three persons, and the evaluation results of two or more persons were employed. The results are presented in Table 3.

Evaluation of Scenting
3: Very good diffusibility of scent
2: Good diffusibility of scent
1: Scent recognized As a result, it was recognized that Example 1 and Example 2, which were dentifrices according to the present invention, exhibit good shape retentivity, have no white residues, and have satisfactory taste and diffusibility of scent Test Example 4 (Examples 3 and 4)

Toothpastes indicated in Table 4 were prepared, and the shape retentivity (toothpaste height, and dripping from the toothbrush) white residues, taste and scents were evaluated in the same manner as in Test Example 3.

TABLE 4

|  | (% by mass) | |
|  | Example 3 | Example 4 |
| --- | --- | --- |
| Calcium carbonate (*1) | 6 | 0.5 |
| Silica (silicic anhydride) 1 | 4 | 8 |
| Sorbitol solution | 42 | 22.5 |
| (70% aqueous solution) |  |  |
| Carboxymethyl cellulose sodium | 2 | 3 |
| Ion-exchanged water | 40 | 60 |
| Polyethylene glycol | 4 | 4 |
| Sodium lauryl sulfate | 1 | 1 |
| Flavor | 1 | 1 |
| Total | 100 | 100 |
| Toothpaste height (mm) | 4.5 | 4.5 |
| Dripping from toothbrush | No dripping | No dripping |
| White residues | Transparent | Transparent |
| Taste | Good | Good |
| Scenting | 2 | 2 |

(*1) Calci F9860 by Sankyo Seifun Co., Ltd.

As a result, it was recognized that Examples 3 and 4 all exhibit good shape retentivity, have no white residues, and have satisfactory taste and scenting ability.

TABLE 3

|  | Example 1 | Example 2 | Comparative Example 1 | Comparative Example 2 | (% by mass) Comparative Example 3 |
| --- | --- | --- | --- | --- | --- |
| Calcium carbonate (*1) | 5 | 5 | — | 10 | — |
| Silica (silicic anhydride) 1 | 5 | 7 | 5 | — | 10 |
| Sorbitol solution | 32 | 30 | 37 | 32 | 32 |
| (70% aqueous solution) |  |  |  |  |  |
| Carboxymethyl cellulose sodium | 2 | 2 | 2 | 2 | 2 |
| Ion-exchanged water | 50 | 50 | 50 | 50 | 50 |
| Polyethylene glycol | 4 | 4 | 4 | 4 | 4 |
| Sodium lauryl sulfate | 1 | 1 | 1 | 1 | 1 |
| Flavor | 1 | 1 | 1 | 1 | 1 |
| Total | 100 | 100 | 100 | 100 | 100 |
| Toothpaste height (mm) | 4.5 | 5.5 | 3 | 2 | 6 |
| Dripping from toothbrush | No dripping | No dripping | Dripping | Markedly dripping | No dripping |
| White residues | Transparent | Transparent | Transparent | Transparent | Remarkable white residues |
| Viscosity (dPa·s) | 1688 | 2500 | 1640 | 280 | 4160 |
| Taste | Good | Good | Good | Good | Powdery |
| Scenting | 3 | 3 | 3 | 3 | 1 |

(*1) Calci F9860 by Sankyo Seifun Co., Ltd.

Dentifrices having the following compositions were prepared, and they all had excellent taste and scent, excellent shape retentivity, and an excellent feeling of use

Example 5

| | |
|---|---|
| Calcium carbonate (*1) | 5 (% by mass) |
| Silica 1 | 6 |
| Silica 2 | 5 |
| Silica 3 | 4 |
| Sorbitol solution (70% aqueous solution) | 32 |
| Water | 42 |
| Xanthan gum | 2 |
| Saccharin sodium | 0.25 |
| Sodium monofluorophosphate | 0.75 |
| Sodium lauryl sulfate | 1.5 |
| Flavor | 1.5 |

(*1) Calci F9860 by Sankyo Seifun Co., Ltd.

Example 6

| | |
|---|---|
| Calcium carbonate (*1) | 0.5 (% by mass) |
| Silica 1 | 9.6 |
| Silica 2 | 3 |
| Silica 3 | 3 |
| Sorbitol solution (70% aqueous solution) | 15 |
| Water | 63 |
| Carrageenan | 3 |
| Sodium lauryl sulfate | 1.5 |
| Flavor | 1.5 |

(*1) Calci F9860 by Sankyo Seifun Co., Ltd.

The invention claimed is:

1. A dentifrice comprising the following components (A), (B) and (C):
   (A) 0.1 to 10% by mass of a thickening silica having an oil absorption of 150 to 500 mL/100 g and an average particle size of 1 to 8μm,
   (B) 0.1 to 8% by mass of heavy calcium carbonate, and
   (C) 40 to 70% by mass of water, wherein the mass ratio (B:A) of the component (B) and the component (A) is 2:1 to 0.5:99.5.

2. The dentifrice according to claim 1, wherein the mass ratio (A: C) of the component (A) and the component (C) is 1:7 to 1:20.

3. The dentifrice according to claim 1, wherein the total amount of the component (A) and the component (B) is 5 to 18% by mass.

4. The dentifrice according to claim 1, wherein the viscosity (25° C.) is 800 to 5000 dPa·s.

5. The dentifrice according to claim 2, wherein the total amount of the component (A) and the component (B) is 5 to 18% by mass.

6. The dentifrice according to claim 2, wherein the viscosity (25° C.) is 800 to 5000 dPa·s.

7. The dentifrice according to claim 3, wherein the viscosity (25° C.) is 800 to 5000 dPa·s.

8. The dentifrice according to claim 5, wherein the viscosity (25° C.) is 800 to 5000 dPa·s.

* * * * *